(12) United States Patent
Leeflang et al.

(10) Patent No.: US 10,856,902 B2
(45) Date of Patent: Dec. 8, 2020

(54) CATHETERS AND DILATORS FOR TRANS-SEPTAL PROCEDURES AND METHODS FOR MAKING AND USING THEM

(71) Applicant: CLPH, LLC, Palo Alto, CA (US)

(72) Inventors: Stephen A. Leeflang, Sunnyvale, CA (US); Christian S. Eversull, Palo Alto, CA (US)

(73) Assignee: CLPH, LLC, Palo Alto, CA (US)

( * ) Notice: Subject to any disclaimer, the term of this patent is extended or adjusted under 35 U.S.C. 154(b) by 288 days.

(21) Appl. No.: 15/723,123

(22) Filed: Oct. 2, 2017

(65) Prior Publication Data

US 2018/0085142 A1 Mar. 29, 2018

Related U.S. Application Data

(63) Continuation of application No. 14/273,509, filed on May 8, 2014, now Pat. No. 9,775,643.

(Continued)

(51) Int. Cl.

| A61B 17/34 | (2006.01) |
|---|---|
| A61L 29/14 | (2006.01) |
| A61B 17/00 | (2006.01) |
| A61M 25/06 | (2006.01) |
| A61M 29/00 | (2006.01) |

(52) U.S. Cl.
CPC .... *A61B 17/3423* (2013.01); *A61B 17/00234* (2013.01); *A61B 17/3403* (2013.01); *A61B 17/3478* (2013.01); *A61L 29/14* (2013.01); *A61M 25/0606* (2013.01); *A61B 17/3417* (2013.01); *A61B 2017/00247* (2013.01); *A61B 2017/00778* (2013.01);

(Continued)

(58) Field of Classification Search
CPC ............ A61B 17/3403; A61B 17/3423; A61B 17/3417; A61B 17/3478; A61B 2017/3409; A61B 17/3454; A61B 17/00247; A61B 17/00778; A61M 25/0606; A61M 29/00
See application file for complete search history.

(56) References Cited

U.S. PATENT DOCUMENTS

| 2003/0078502 A1* | 4/2003 | Miyaki ................ A61B 8/0833 600/461 |
| 2012/0179188 A1* | 7/2012 | Chanduszko ...... A61B 17/0057 606/185 |
| 2013/0274784 A1* | 10/2013 | Lenker ............. A61B 17/32053 606/185 |

FOREIGN PATENT DOCUMENTS

JP 2008011867 A * 1/2008

* cited by examiner

*Primary Examiner* — Ashley L Fishback
(74) *Attorney, Agent, or Firm* — Vista IP Law Group LLP; William A. English (57) ABSTRACT

Devices and methods are provided for performing a medical procedure using a trans-septal approach. The device includes a dilator including a proximal end, a distal end terminating in a distal tip, and a lumen extending between the dilator proximal and distal ends, and a needle device including a proximal end, a distal end sized for introduction into the dilator lumen and terminating in a sharpened distal tip. The needle is movable relative to the dilator to selectively expose the needle device distal tip distally from the dilator lumen and advance the dilator relative to the needle device. The dilator may have a complex tapered shape on its distal tip, e.g., including first and second tapered regions. The needle device may include an inner needle including the sharpened distal tip and an outer tube including a substantially blunt distal end that slidably receives the inner needle.

17 Claims, 10 Drawing Sheets

Related U.S. Application Data (60) Provisional application No. 61/820,993, filed on May 8, 2013, provisional application No. 61/912,503, filed on Dec. 5, 2013.

(52) U.S. Cl.
CPC ........... *A61B 2017/3409* (2013.01); *A61B 2017/3454* (2013.01); *A61L 2400/10* (2013.01); *A61M 29/00* (2013.01)

CATHETERS AND DILATORS FOR TRANS-SEPTAL PROCEDURES AND METHODS FOR MAKING AND USING THEM

RELATED APPLICATION DATA

This application is a continuation of co-pending application Ser. No. 14/273,5099, filed May 8, 2014, and issuing as U.S. Pat. No. 9,775,643, which claims benefit of provisional application Ser. No. 61/820,993, filed May 8, 2013, and 61/912,503, filed Dec. 5, 2013, the entire disclosures of which are expressly incorporated by reference herein.

FIELD OF THE INVENTION

The present invention relates generally to apparatus, systems, and methods for performing medical procedures, and, more particularly, to dilators, needles, and access devices for accessing a body lumen within a patient's body, and to methods for making and using such devices.

BACKGROUND

Various medical procedures involve accessing a chamber of the heart using a trans-septal approach. For example, a guide catheter or sheath may be introduced into the right atrium of a patient's heart, e.g., from a percutaneous access site, and a Brockenbrough needle may be introduced through the guide sheath and advanced through the intra-atrial septum of the heart into the left atrium. A guidewire may be then introduced through the needle into the left atrium, whereupon the needle may be removed.

One or more dilators may be advanced over the guidewire (or over the needle before removal) to dilate the puncture through the septum, e.g., to create a passage sufficiently large to introduce the guide sheath through the puncture in the septum. The dilator provides a transition to bridge the diameter difference between the guidewire and the outer diameter of the guide sheath. The taper provided on the tip of such dilators is generally a substantially uniform conical ramp, and the longer the taper (i.e., the more shallow the angle), the lower the axially-applied axial force needed to apply the same radial dilation force against the tissue surrounding the puncture.

However, if the length of dilator tip is too long, it may present a safety risk, such as left atrial perforation or other damage to tissue. For example, a dilator taper may be too long for a number of reasons including 1) it is so long that it touches undesired anatomy before the guide sheath can access the desired space (e.g., the left atrial wall, vessel bifurcation, and the like) or 2) in the follow-through that frequently happens (e.g., when the insertion force drops dramatically when fully dilated to the sheath diameter) the dilator tip may touch and/or damage undesired anatomy.

One or more instruments may then be introduced through the guide sheath and/or over the guidewire into the left atrium, e.g., to perform a procedure within the left atrium or other region of the heart accessed via the left atrium.

Additionally, there is a need for devices that facilitate accessing body lumens, such as chambers of the heart using trans-apical approaches and/or other puncture techniques, e.g., to perform medical procedures therein, while reducing the risk of undesired punctures or tissue damage.

SUMMARY

The present invention is directed to apparatus, systems, and methods for performing medical procedures. More particularly, the present invention is directed to dilators, needles, and access devices for accessing a body lumen within a patient's body, e.g., accessing a chamber of the heart across a septum of the heart, to systems including such devices, and to methods for making and using such devices.

In an exemplary embodiment, a method is provided for performing a medical procedure within a patient's body, e.g., involving accessing a chamber of the heart using a trans-septal approach. Generally, a distal end of a tubular sheath is introduced into a first body lumen, e.g., into the right atrium or other chamber of the patient's heart, and a needle device may be used to puncture a septum or other tissue wall to create a puncture therethrough communicating with a second body lumen, e.g., the left atrium or other adjacent chamber of the heart. A dilator may be advanced over the needle device through the tissue wall, thereby dilating tissue surrounding the puncture, and a procedure sheath, e.g., the tubular sheath, may be advanced over the dilator through the dilated puncture into the second body lumen. Optionally, a guidewire may be introduced through the puncture, e.g., via the needle device, the dilator, and/or the sheath. One or more instruments may be introduced through the sheath into the second body lumen to perform a medical procedure.

When the dilator is advanced through the puncture, the tissue dilation forces applied to the tissue surrounding the puncture, as a function of diameter, may not be linear. Generally speaking, tissue dilation forces are, on average, smallest in the initial semi-elastic range of the tissue and increase non linearly outside of the initial elastic range. In an exemplary embodiment, the tip of the dilator may include a taper configuration to facilitate advancement and/or minimize "jumping" (when the dilator tip clears the tissue, which may otherwise cause the distal tip to advance suddenly into the second body lumen). For example, the dilator tip may include multiple tapered regions having different taper angles, e.g., a relatively steep initial tapered region at the distal-most region of the tip, and a longer and/or relatively smaller tapered region proximal to the distal-most region. For example, the dilator tip may be configured to provide a substantially consistent "axial dilation force," i.e., the linear pushing encountered by the operating physician may be substantially constant as the dilator tip is advanced through the tissue to dilate the puncture.

In accordance with another embodiment, an access device is provided that includes a dilator comprising a proximal end, a distal end sized for introduction into a patient's body and terminating in a distal tip having a complex tapered shape, and a lumen extending between the dilator proximal and distal ends; and a needle device comprising a proximal end, a distal end sized for introduction into the dilator lumen and terminating in a sharpened distal tip, the needle movable relative to the dilator to selectively expose the needle device distal tip distally from the dilator lumen and advance the dilator relative to the needle device. In one embodiment, the dilator distal tip may include a distal-most region have a first linear taper defining a first angle relative to a longitudinal axis of the dilator, and a second region adjacent the distal-most region having a second liner taper defining a second angle relative to the longitudinal axis, the second angle being smaller than the first angle. In another embodiment, the dilator distal tip may include a continuously variable curved taper.

In accordance with yet another embodiment, a method is provided for performing a medical procedure within a patient's body that includes introducing a distal end of a tubular sheath into a first body lumen; advancing a distal end of a needle device from the distal end of the sheath through a tissue wall into a second body lumen; advancing a distal end of a dilator over the needle device through the tissue wall, thereby dilating tissue surrounding the puncture using a complex shaped tapered distal tip of the dilator; and advancing the sheath distal end over the dilator through the dilated puncture into the second body lumen. In an exemplary embodiment, the complex shaped tapered distal tip may be shaped to provide a substantially consistent axial dilation force when the complex shaped tapered distal tip is advanced through the tissue wall to dilate the puncture.

In accordance with still another embodiment, an access device is provided for performing a medical procedure using a trans-septal approach that includes a dilator comprising a proximal end, a distal end sized for introduction into a patient's body and terminating in a tapered distal tip, and a lumen extending between the dilator proximal and distal ends; an outer tube comprising a proximal end, a distal end sized for introduction into the dilator lumen and terminating in a substantially blunt distal tip, and a lumen extending between the outer tube proximal and distal ends; and a needle comprising a proximal end, a distal end sized for introduction into the outer tube lumen and terminating in a sharpened distal tip, wherein the needle is movable relative to the outer tube to selectively expose the needle distal tip distally from the outer tube lumen and retract the needle distal tip into the outer tube lumen, and wherein the dilator is movable relative to the outer tube for advancing the dilator distal tip relative to the outer tube.

In accordance with another embodiment, a system is provided for performing a medical procedure using a trans-septal approach that includes a tubular sheath comprising a proximal end, a distal end sized for introduction into a patient's body, and a lumen extending between the sheath proximal and distal ends; a dilator comprising a proximal end, a distal end sized for introduction into the sheath lumen and terminating in a tapered distal tip, and a lumen extending between the dilator proximal and distal ends; an outer tube comprising a proximal end, a distal end sized for introduction into the dilator lumen and terminating in a substantially blunt distal tip, and a lumen extending between the outer tube proximal and distal ends; and a needle comprising a proximal end, a distal end sized for introduction into the outer tube lumen and terminating in a puncturing distal tip, wherein the needle is movable relative to the outer tube to selectively expose the needle distal tip distally from the outer tube lumen and retract the needle distal tip into the outer tube lumen, and wherein the dilator is movable relative to the outer tube and the sheath for advancing the dilator distal tip relative to the outer tube.

In accordance with still another embodiment, a method is provided for performing a medical procedure within a patient's body that includes introducing a distal end of a tubular sheath into a first body lumen; advancing a distal end of an outer tube from the distal end of the sheath within the first body lumen; pressing the outer tube distal end against a tissue wall within the first body lumen; with an inner needle positioned within the outer tube such that a sharpened distal tip of the needle is positioned adjacent the outer tube distal end and the tissue wall, retracting the outer tube, thereby impaling the tissue wall on the sharpened distal tip and directing the sharpened distal tip through the tissue wall into a second body lumen and creating a puncture through the tissue wall; and advancing the outer tube distal end over the needle through the puncture and into the second body lumen.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which:

FIGS. 6A(1)-6B(2) are graphs comparing forces experienced when using the distal tips of FIGS. 6A and 6B to dilate a puncture through tissue.

DETAILED DESCRIPTION OF THE EXEMPLARY EMBODIMENTS

Figure 1:
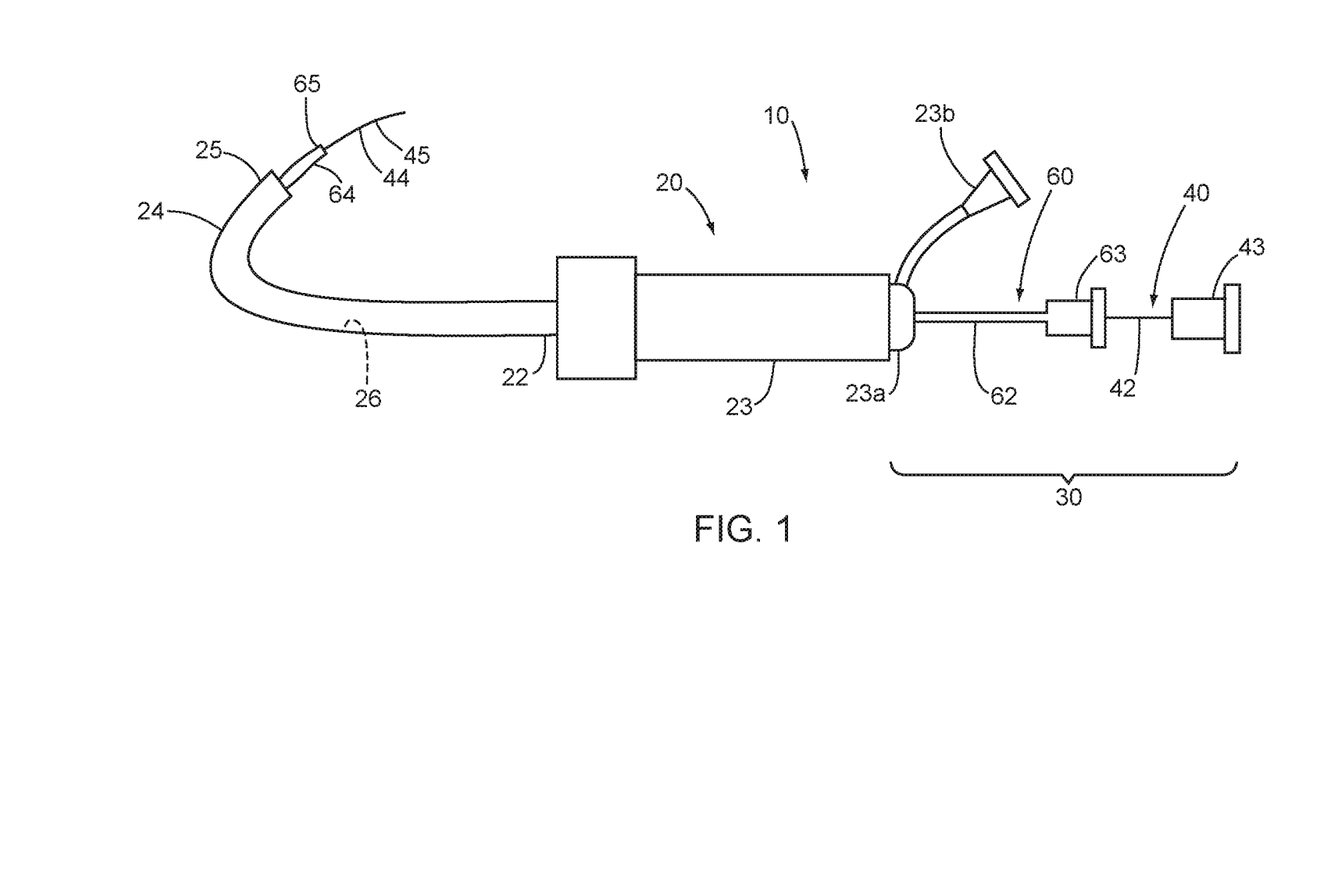
FIG. 1 is a perspective view of an exemplary embodiment of a system for performing a medical procedure using a trans-septal approach that includes a guide sheath, dilator, and needle device.

Turning to the drawings, FIG. 1 shows an exemplary embodiment of a system 10 for performing a diagnostic and/or therapeutic procedure within a patient's body, e.g., within a chamber of a heart accessed using a trans-septal approach. In the embodiment shown, the system 10 includes a guide sheath, catheter, or other tubular member 20, e.g., for introducing one or more devices into a patient's body to perform a procedure, and a trans-septal access device 30 that may be introduced through the guide sheath 20, e.g., to puncture or otherwise penetrate through a tissue structure to provide access to a body lumen beyond the tissue structure, e.g., to access a chamber of a heart from an adjacent chamber, as described further below. Generally, the access device 30 includes a needle device 40 and a dilator 60 slidable relative to one another, such as any of the embodiments described elsewhere herein.

Figure 2:
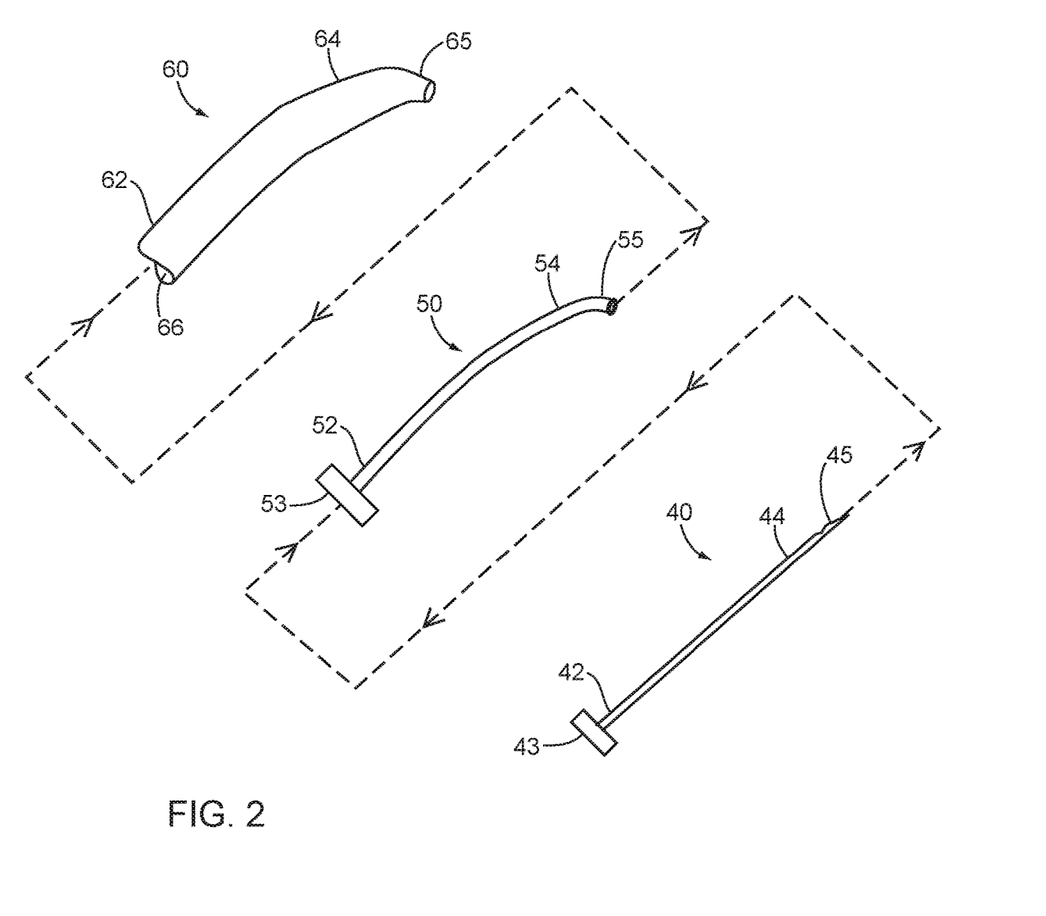
FIG. 2 is an exploded view of an exemplary embodiment of an access device that may be included in the system of FIG. 1 in which the needle device includes an inner needle and an outer tube.

FIG. 2 shows an exemplary embodiment of an access device 30 that may be used in conjunction with the guide sheath 20, which includes an inner needle 40, an outer tube 50, and a dilator 60, which may telescoped relative to one another, i.e., allowing the needle 40 to be removably inserted into the outer tube 50, and the outer tube 50 to be removably inserted into the dilator 60, allowing the components of the access device 30 to remain slidable relative to one another during a procedure.

The components of the system 10, e.g., the guide sheath 20, needle 40, outer tube 50, and dilator 60, may have lengths sufficient to be introduced from an access site, e.g., a percutaneous access site into the patient's vasculature, into a target body lumen, e.g., the right atrium or other chamber of the heart. The relative lengths of the components may allow tips of the needle 40, outer tube 50, and/or the dilator 60 to be exposed a desired distance and/or retracted into the surrounding device, as described further below. In exemplary embodiments, the components of the system 10 may have a length between about twenty and one hundred twenty centimeters (20-120 cm) with the lengths varying relative to one another by a predetermined distance, e.g., to allow distal tips of the components to be deployed from the surrounding component a desired distance during use. Optionally, one or more of the components may include stops and/or other features, which may limit relative movement of the telescoped components relative to one another, e.g., on or in the distal ends and/or on the handles or hubs (not shown), as described elsewhere herein.

The inner needle 40 is generally an elongate solid or hollow needle including a proximal end 42 with a hub or handle 43, a distal end 44 terminating in a sharpened distal tip 45, thereby defining a longitudinal axis 12 therebetween. Optionally, the needle 40 may include a guidewire lumen (not shown) extending between the proximal and distal ends 42, 44, e.g., to allow a guidewire or other rail (also not shown) to be advanced through the needle 40, e.g., after puncturing the septum to allow the rail to be introduced into a target chamber beyond the septum.

In exemplary embodiments, the distal tip 45 may be pointed, beveled, and/or otherwise sharpened to allow the distal tip 45 to puncture through tissue, such as the intra-atrial septum (not shown), as described elsewhere herein. Alternatively, the distal tip 45 and/or distal end 44 adjacent the distal tip 45 may include one or more features to facilitate puncturing and/or other otherwise directing the distal tip 45 through tissue. For example, one or more helical threads (not shown) may be provided along a desired length of the distal end 44 from the distal tip 45, e.g., to allow the distal tip 45 to be threaded into and through tissue and/or unthreaded back through the tissue, as desired.

The needle 40 may be formed from metal, e.g., stainless steel, and/or other materials having sufficient column strength to allow the distal tip 45 to be advanced to puncture tissue from the proximal end 42 without buckling or kinking. For example, the needle 40 may be formed from a single solid or tubular wire, hypo-tube, and the like having a substantially uniform diameter or other cross-section along its length and/or having a variable cross-section along its length. The distal end 44 of the needle 40 may be biased to a substantially straight configuration, yet may be resiliently directed into a curved or other shape, e.g., when positioned with the outer tube 50 and/or other components of the access device 30.

The outer tube 50 may be constructed generally similar to the needle 40, e.g., including a proximal end 52 (optionally, including a hub or handle 53), a distal end 54 sized for introduction into the guide sheath 20, and a lumen 56 extending therebetween sized for slidably receiving the needle 40. Unlike the needle 40, the outer tube 50 may terminate in a substantially blunt distal tip 55 and/or may include one or more elements (not shown) on the distal tip 55 for releasably biting into or otherwise engaging tissue without puncturing entirely through the tissue. Alternatively, the distal tip 55 may be formed from relatively soft and/or atraumatic material, e.g., to prevent the distal tip 55 from puncturing and/or otherwise damaging tissue when the distal tip 55 is pressed or otherwise directed against tissue, as described further elsewhere herein.

In exemplary embodiments, the outer tube 50 may formed from a stainless steel hypo-tube or other tubular body, e.g., having sufficient column strength to allow the distal tip 55 to be pressed against tissue, e.g., to cause the septum to tent or be subjected to tension to facilitate puncturing the septum using the needle 40, as described elsewhere herein. Optionally, as shown, the distal end 54 of the outer tube 50 may be bent, curved, or biased to other non-linear shapes, e.g., immediately adjacent the distal tip 55, yet may be resiliently straightened, e.g., when positioned within the dilator 60 and/or guide sheath 20 during introduction. In an alternative embodiment, the outer tube 50 may be omitted and the needle 40 may be provided directly within the dilator 60 or the dilator 60 may be advanced directly over the needle 40 without any intervening devices therebetween.

The dilator 60 is also a generally tubular member including a proximal end 62, a distal end 64, and a lumen 66 extending therebetween. The dilator 60 may terminate in a substantially atraumatic distal tip 65, e.g., including a predetermined taper or other shape, as described elsewhere herein. In addition or alternatively, the distal end 64 of the dilator 60 may include a predetermined curve, bend, and/or other non-linear shape, yet may be resiliently straightened, bent further, and the like, for example, to facilitate introduction of the dilator 60, e.g., through tortuous anatomy and/or over the needle 40 and/or outer tube 50.

Optionally, the dilator 60 may include one or more markers (not shown) on the distal end 64, e.g., to facilitate positioning and/or otherwise monitoring the dilator 60 using external imaging, such as fluoroscopy, ultrasound, and the like. In an exemplary embodiment, a plurality of markers may be provided on the distal end 64 that are spaced apart axially from one another. If the distal end 64 includes a curve or bend, the markers may be arranged asymmetrically relative to the periphery of the distal end 64, e.g., to facilitate identifying the rotational orientation of the distal end 64 using external imaging. For example, a plurality of markers may be provided on only one side of the distal end 64, e.g., on the outside of the bend or curve, to identify the location and orientation of the distal end 64.

The dilator 60 may be formed from various materials, such as polymers or other plastics, e.g., HDPE, UHMWPE, PTFE, Nylon, harder grades of PEBA, urethanes, and the like. Optionally, one or more coatings, e.g., of hydrophilic, silicone, and/or other materials may be provided along the inner surface defining the lumen 66 and/or along at least part of the outer surface, e.g., to facilitate introduction of the needle 40 and/or outer tube 50 therethrough and/or sheath 20 thereover. Alternatively, the dilator 60 may be formed from multiple layers and/or segments of materials having different mechanical properties than one another and/or may include a liner, e.g., a hydrophilic or lubricious material and/or a braid or coil of metal or polymeric material, that may reduce the risk of the needle 40 and/or outer tube 50 skiving or otherwise damaging the inner surface, e.g., similar to other embodiments herein.

Returning to FIG. 1, the guide sheath 20 may be any conventional catheter or sheath including a proximal end 22, a distal end 24 sized for insertion into a body lumen, a lumen 26 extending between the proximal and distal ends 22, 24, and a central longitudinal axis 28 extending between the proximal and distal ends 22, 24. The lumen 26 may exit at or communicate with an outlet 27 in the distal end 24, e.g., to allow the access device 30, a guidewire, and/or other instrument (not shown) to be introduced therethrough. The distal end 24 may include a tapered, rounded, or otherwise shaped distal tip 25, e.g., to provide a substantially atraumatic tip and/or to facilitate advancement or navigation through various anatomy.

Optionally, the proximal end 22 may include a handle or hub 23, e.g., configured and/or sized for holding and/or manipulating the guide sheath 20 from the proximal end 22. In addition, the handle 23 may include one or more ports, e.g., a port 23a communicating with the lumen 26 and including one or more valves, e.g., a hemostatic valve (also not shown), which may provide a substantially fluid-tight seal, while accommodating insertion of one or more instruments into the lumen 26. In addition, as shown, the handle 23 may include an infusion port 23b, e.g., for coupling a source of fluid (not shown) to the handle 23 to deliver saline or other fluids into the lumen 26, e.g., around the dilator 60, needle 40, and/or other instruments (not shown) positioned within the lumen 26.

Generally, the guide sheath 20 may include an inner liner, e.g., at least partially or entirely surrounding or otherwise defining the lumen 26, a reinforcement layer surrounding the inner liner, and an outer jacket surrounding the reinforcement layer, each of which may extend at least partially between the proximal and distal ends 22, 24 of the guide sheath 20. The reinforcement layer and/or outer jacket may be attached to the inner liner, e.g., by laminating, adhering, adhesive bonding, ultrasonic welding, reflowing or other heating, and the like, as described elsewhere herein.

In an exemplary embodiment, the lumen 26 is defined by an inner liner including an inner surface, e.g., formed from lubricious material. Alternatively, the inner liner may be formed from one or more layers of thermoplastic or other polymeric material including one or more coatings on the inner surface having desired properties, e.g., a hydrophilic and/or lubricious coating, e.g., similar to the liners disclosed in U.S. Pat. Nos. 7,550,053 and 7,553,387, and U.S. Publication No. 2009/0126862, the disclosures of which are expressly incorporated by reference herein.

Optionally, any or all of the inner liner, reinforcement layer, and/or outer jacket may be formed from multiple layers of like or different materials (not shown), e.g., to provide desired material properties in the different portions of the guide sheath 20. In an exemplary embodiment, the outer jacket may be formed from PEBAX, nylon, urethane, and/or other thermoplastic material, e.g., such that the material of the outer jacket 44 may be heated and reflowed and/or otherwise formed around the components defining the lumen 18.

In one embodiment, one or more of the layers of the guide sheath 20 may have a substantially homogenous construction between the proximal and distal ends 22, 24. Alternatively, the construction may vary along the length of the guide sheath 20 to provide desired properties. For example, a proximal portion of the guide sheath 20 adjacent the proximal end 12 may be substantially rigid or semi-rigid, e.g., providing sufficient column strength to allow the distal end 14 of the guide sheath 20 to be pushed or otherwise manipulated from the proximal end 22, while a distal portion may be substantially flexible.

The reinforcement layer may include one or more reinforcing members, e.g., wound in a braided or other helical configuration around the inner liner, and the outer jacket may include one or more tubular layers surrounding the reinforcement layer and/or between the reinforcement layer and the inner liner. In an exemplary embodiment, the reinforcement layer may include one or more, or a plurality of, round or flat (e.g., rectangular, elliptical, or flat oval) wires, filaments, strands, or other reinforcement members, e.g., formed from metal, such as stainless steel, plastic, glass, woven or twisted fibers, such as aramid, and the like, or composite materials.

Figure 3A:
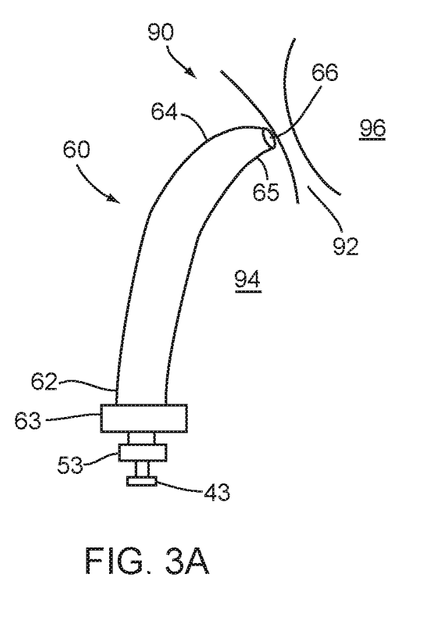
FIGS. 3A-3D are cross-sectional views of a patient's heart showing a method for accessing a chamber of the heart trans-septally using the access device of FIG. 2.

Turning to FIGS. 3A-3D, an exemplary method is shown for using the access device 30 of FIG. 2 to provide transseptal access within a patient's heart 90, e.g., across the intra-atrial septum 92 between chambers of the heart 90, for example, from the right atrium 94 into the left atrium 96. Initially, as shown in FIG. 3A, the distal end 24 of the guide sheath 20 may be introduced into the patient's body, e.g., into the patient's vasculature from a percutaneous access site in a femoral vein, left or right internal or external jugular vein, subclavian vein, axillary vein, and the like. For example, the distal end 24 may be advanced and/or otherwise manipulated until the distal tip 25 is positioned within the right atrium 94 adjacent the septum 92, e.g., adjacent a target puncture site to access the left atrium 96.

The needle 40, outer tube 50, and dilator 60 may be preloaded within the lumen 26 of the guide sheath 20 with the distal tips 45, 55, 65 positioned within the lumen 26, e.g., adjacent the distal tip 27 of the guide sheath 20 during introduction of the guide sheath 20. Alternatively, the needle 40, outer tube 50, and/or dilator 60 may inserted into the guide sheath 20 after positioning the distal end 24 within the right atrium 94. In this alternative, the dilator 60 may be inserted first and then the needle 40 and outer tube 50 may be inserted into the dilator 60 together or sequentially.

If the outer tube 50 and needle 40 are introduced together into the dilator 60 or guide sheath 20, the outer tube 50 may protect the inner surface of the dilator lumen 66 and/or guide sheath lumen 26. For example, the needle tip 45 may be positioned within the outer tube lumen 54 adjacent the outer tube tip 55, and the needle 40 and outer tube 50 may be inserted together into the dilator lumen 64. In this configuration, the outer tube 50 covers the needle tip 45, preventing the needle tip 45 from contacting the inner surface, which may otherwise skive and/or remove pieces of the dilator 60 and/or guide sheath 20, which may be released into the right atrium 94 where they may risk substantial harm to the patient.

Figure 3B:
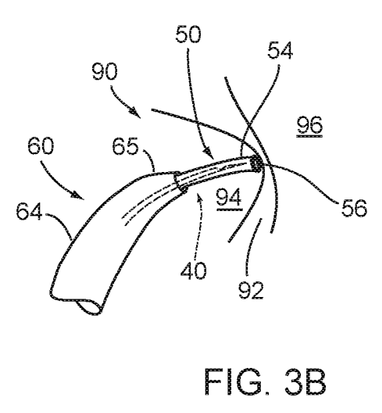

Turning to FIG. 3B, with the distal tip 25 of the guide sheath 20 adjacent the septum 92, the outer tube 50 may be advanced, e.g., to deploy the distal end 54 of the outer tube 50 within the right atrium 94 and/or press the distal tip 55 against the septum 92, e.g., to cause the tissue of the septum 92 to "tent" or otherwise become subjected to tension away from the right atrium 94, as shown. Optionally, the distal tip 55 may otherwise engage the wall of the right atrium 94 without puncturing the septum 92, e.g., to couple the outer tube 50 to the septum 50.

Figure 3C:
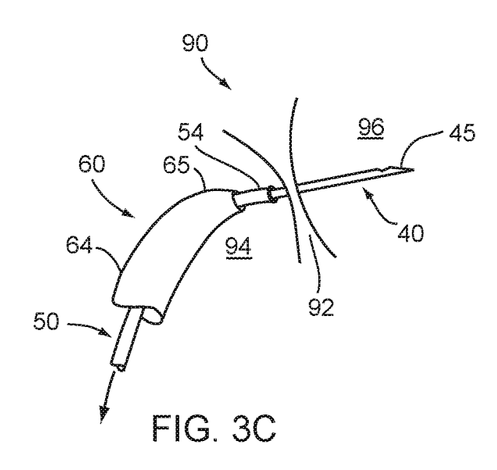

With reference to FIG. 3C, the needle 40 may be positioned such that the distal tip 45 is immediately adjacent the distal tip 55 of the outer tube 50 (if not already positioned at this location), and the outer tube 50 may be retracted proximally. This action may reveal or expose the distal tip 45 of the needle 40 from the outer tube 50 and pull the septum 92 proximally and/or permit the release of built up tension in the septum 92, thereby causing the septum 92 to impale over the distal tip 45 and/or driving the distal end 44 of the needle 40 through the septum 92, e.g., until the distal end 44 enters the left atrium 96. Thus, in this method, the needle 40 may not be advanced to puncture the septum 92, e.g. but the needle 40 remains substantially stationary while the septum 92 moves from left to right onto and/or over the needle 40, which may reduce the risk of over-advancement or "jumping" of the needle 40 and/or undesired movement of the tissue.

Figure 3D:
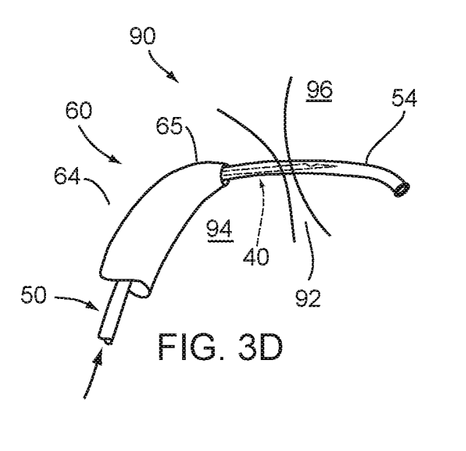

Optionally, the outer tube 50 may be advanced over the needle 40 to direct the distal end 54 of the outer tube 50 through the puncture in the septum 92 into the left atrium 96. The needle 40 may then be removed, leaving the distal end 54 of the outer tube 50 within the left atrium 96 to provide subsequent access. Thus, given that the distal tip 55 of the outer tube 50 does not include a sharp, puncturing tip like the needle 40, a sharp object is not presented within the left atrium 96 for the subsequent steps of the procedure, which may reduce the risk of injury to tissue within the left atrium 96. Optionally, the distal end 54 and/or distal tip 55 may be made soft or compliant, e.g., by a laser cut pattern, material transition, addition of a polymer tip, and the like. Alternatively, the distal end 54 and/or distal tip 55 may include a shape, e.g., to cause it to be less traumatic and/or anchor after crossing into the left atrium 96, e.g., such as a coil, helix and/or bend (not shown). One or more devices (not shown) may be delivered and or monitoring performed, e.g., pressure transduction, and the like through the lumen 56 of the outer tube 50.

In addition or alternatively, a guidewire (not shown) may be introduced through the access device 30 into the left atrium, e.g., through the needle 40 if it includes a guidewire lumen or through the lumen 56 of the outer tube 50 after removing the needle 40. Optionally, once the tip of the guidewire is positioned within the left atrium 96, the outer tube 50 may be removed, thereby leaving the guidewire extending from the guide sheath 20 through the puncture in the septum 92 into the left atrium 96.

The dilator 60 may then be introduced into the guide sheath 20 (or simply advanced if already positioned within the guide sheath 20), e.g., over the guidewire, or alternatively over the outer tube 50 and/or needle 40 if not removed. The distal end 64 of the dilator 60 may be exposed from the guide sheath 20 within the right atrium 94 and advanced into the puncture to dilate the tissue of the septum 92 surrounding the puncture. Optionally, the tapered shape of the distal tip 65 of the dilator may be selected to facilitate insertion through the septum 92 and/or dilation of tissue without substantial risk of jumping or other over-advancement of the dilator 60 when the distal end 64 clears the septum 92 and enters the left atrium 96, e.g., as described further elsewhere herein.

As described elsewhere herein, the dilator 60 may provide a transition from the relatively small outer diameter or profile of the guidewire (or outer tube 50 or needle 40 if not removed) to the relatively larger outer diameter or profile of the guide sheath 20. Thus, once the larger diameter region of the distal end 64 of the dilator 60 is advanced completely through the septum 92 into the left atrium 96, the puncture may be dilated to a diameter substantially similar to the outer profile of the guide sheath 20 (or alternatively another procedure sheath, not shown, which may be advanced through the guide sheath 20 or may replace the guide sheath 20). The guide sheath 20 may then be advanced through the septum 92 to position the distal tip 25 of the guide sheath 20 within the left atrium 96. The dilator 60 (and outer tube 50 or needle 40 if not already removed) may then be withdrawn into the guide sheath 20 and removed completely from the patient's body.

With the guide sheath 20 and/or guidewire positioned within the left atrium 96, the sheath lumen 26 may then be used to introduce one or more instruments (not shown) into the left atrium 96 to perform one or more procedures within the left side of the heart, e.g., within the left atrium 96 itself or the left ventricle (not shown). Once the desired procedure(s) are completed, the instrument(s) may be removed and then the guide sheath 20 and guidewire may also be removed. The puncture in the septum 92 may be closed using conventional devices and methods, e.g., via the guide sheath 20 and/or guidewire before their removal.

Figure 4A:
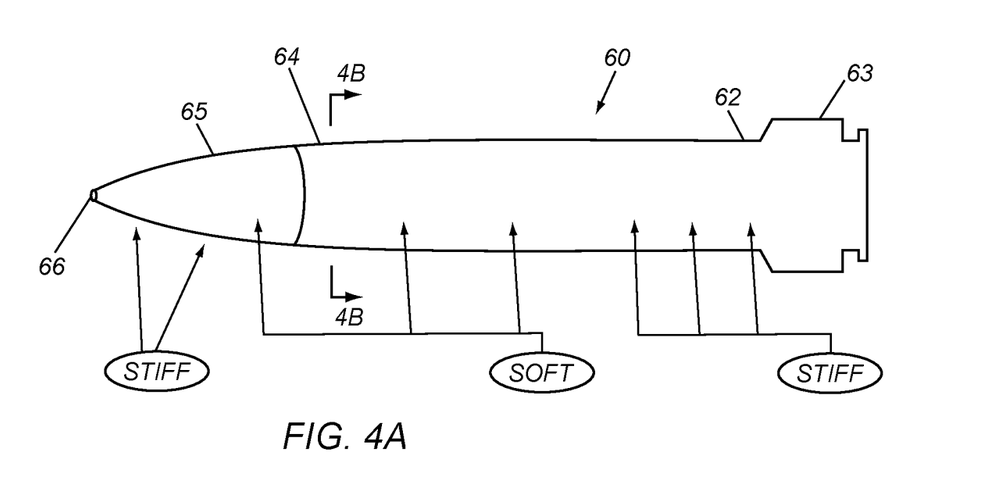
FIG. 4A is a side view of an exemplary embodiment of a dilator.
Figure 4B:
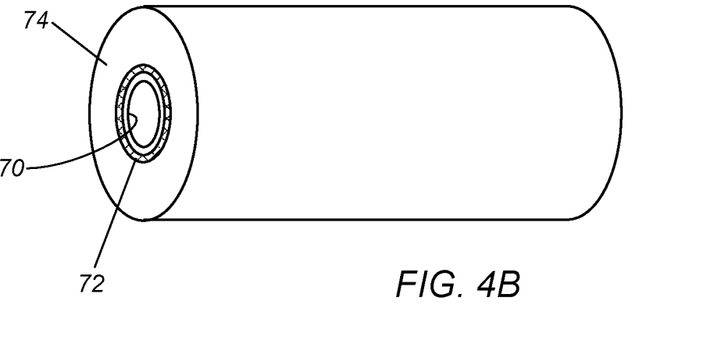
FIG. 4B is a partial cross-sectional view of a region of the dilator of FIG. 4A showing an exemplary construction of the dilator.

Turning to FIGS. 4A and 4B, an exemplary embodiment of a dilator 60 is shown, which may be included in the access device 20 and/or system 10 (not shown) described elsewhere herein. In the embodiment shown, the dilator 60 is formed from different materials having different material properties, e.g., at different locations along the length of the dilator 60 and/or in different layers of the dilator 60.

For example, as shown in FIG. 4A, the dilator 60 may be configured to provide different stiffnesses at different axial locations on the dilator 60, e.g., a proximal end 62 that is substantially rigid and/or semi-rigid to facilitate advancement of the distal end 64 without substantial risk of the dilator 60 buckling or kinking. In addition, a distal-most region of the tapered distal tip 65 may also be formed from substantially rigid, semi-rigid, or relatively stiff material, e.g., to ensure that the distal-most region holds its shape when advanced through tissue, e.g., surrounding a septal puncture, at a percutaneous access site, and the like. A proximal region of the tapered distal tip 65 and/or a predetermined length of the distal end 64 may be formed from flexible and/or relatively soft material, e.g., to allow the distal end 64 to bend during introduction through tortuous anatomy. Optionally, a further proximal region (not shown) may be formed from a relatively stiffer material to provide pushability and/or support.

In addition or alternatively, as shown in FIG. 4B, the dilator 60 may be formed from a plurality of layers having different mechanical properties. For example, the dilator 60 may include a relatively thin inner layer 70 of relatively hard and/or abrasion resistant material, e.g., HDPE, UHMWPE, PTFE, nylon, harder grades of PEBA or urethanes, and the like, surrounded by a relatively thick outer layer 74 of relatively soft material, e.g., PEBAX, urethane, and the like. Optionally, as shown, an intermediate bond layer 72, e.g., to enhance bonding the inner and outer layers 70, 74 together, e.g., including Plexar, Oravec, and the like. Alternatively, the inner and outer layers 70, 74 may be attached directly to one another, e.g., by one or more of melting, reflowing, sonic welding, heat welding, and the like.

In one embodiment, the inner layer 70 may extend substantially the entire length of the dilator 60, e.g., entirely between the proximal and distal ends 62, 64, while one or more material may be used for the outer layer 74, e.g., to vary the rigidity/flexibility along its length. The inner layer 70 may provide desired stiffness and/or abrasion resistance to protect the inner surface of the dilator 60, e.g., when a needle device (not shown) is introduced through the dilator lumen 66, thereby reducing the risk of skiving and/or removing pieces of the dilator 60, e.g., when a sharpened tip of a needle is advanced through the dilator lumen 60, particularly if the dilator 60 is positioned in a curved or other nonlinear orientation within a patient's anatomy. In particular, HDPE may provide a substantially low friction surface for use as a liner for a dilator 60 used with a stainless steel needle that prevents substantial risk of skiving.

The outer layer 74 may increase the flexibility of the dilator 60, e.g., compared to forming the dilator 60 entirely from HDPE or other relatively stiff materials. Using relatively softer, flexible materials for the outer layer 74 may enhance pushability of the dilator 60, e.g., through tortuous anatomy. In exemplary embodiments, the inner layer 70 may have a thickness between about 0.001 to 0.025 inch (0.025-0.625 mm) and the outer layer 74 may have a thickness substantially greater than the inner layer 70, e.g., between about 0.005 to 0.15 inch (0.125-3.75 mm).

Optionally, the inner surface of the inner layer 70 may be coated with one or more materials, e.g., a silicone, hydrophilic, and/or other coating, as described elsewhere herein for other embodiments, to reduce friction and/or otherwise facilitate inserting needle devices through the dilator 60. In addition or alternatively, the inner layer 70 may include one or more additional structures, e.g., a braid or coil of metal or polymeric material, which may be substantially abrasion resistant and/or reduce friction for devices inserted through the dilator 60.

Figure 5A:
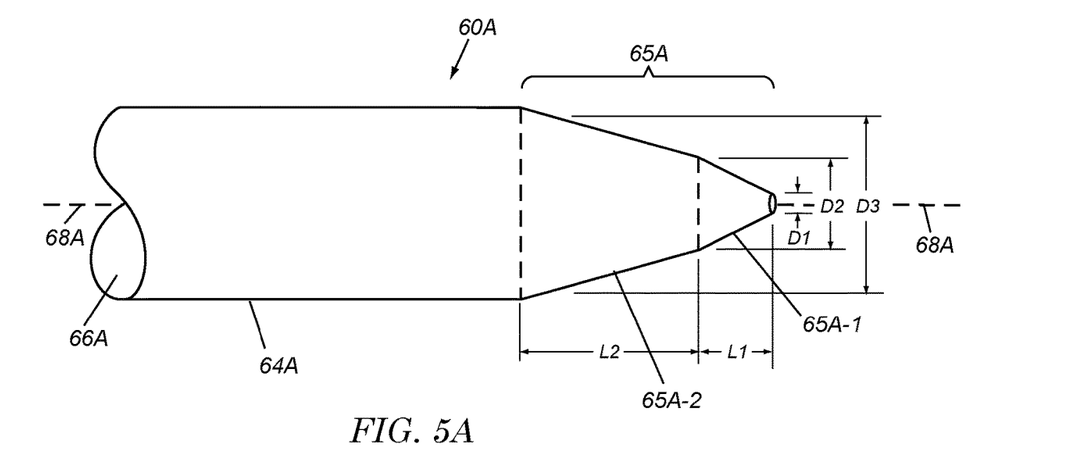
FIGS. 5A and 5B are details showing exemplary distal tips that may be provided on a dilator, such as that shown in FIG. 4A.
Figure 5B:
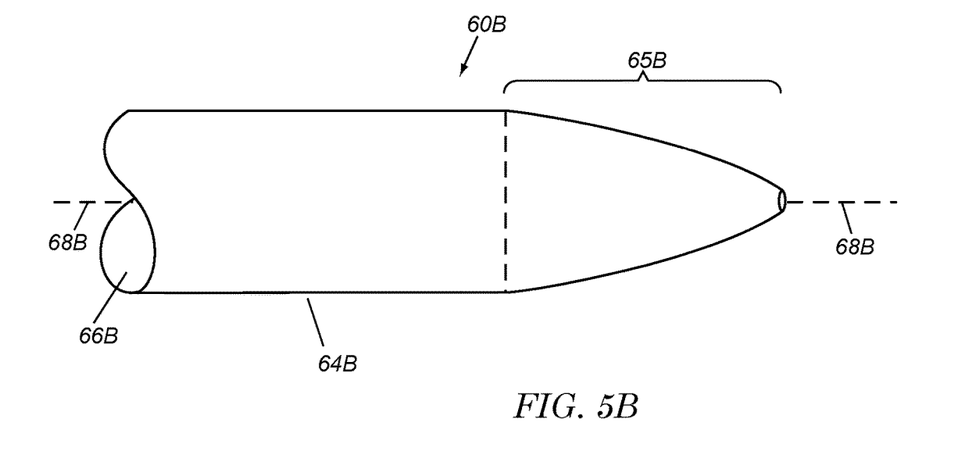

Turning to FIGS. 5A and 5B, any of the dilators herein may include a tapered distal end having a complex shaped taper, e.g., designed to transform non-linear tissue dilation function for a given tissue into a substantially more constant axial dilation force, e.g., for one or more of the benefits described elsewhere herein, within a given length constraint. For example, FIG. 5A shows an exemplary embodiment of a distal end 64A of a dilator 60A that includes a tapered distal tip 65A including two substantially linear tapers. As shown, the tapered distal tip 65A includes a distal-most region 65A-1 having a first taper of a relatively steep angle relative to a longitudinal axis 68 and an adjacent region 65A-2 having a second taper of a more shallow angle. For example, in the embodiment shown, the distal-most region 65A-1 may have a length L1 and transition from a smallest diameter D1 to an intermediate diameter D2, and the adjacent region 65A-2 may have a length L2 and transition from the intermediate diameter D2 to an outer diameter D3 of the dilator 60A. Thus, in this embodiment, the tapers may be configured such that (D2−D1)/L1 is greater than (D3−D2)/L2, while L1+L2 may be less than or equal to the total length of a simple/conventional dilator taper while maintaining or reducing axial puncture force, e.g., to reduce the risk of damaging tissue within a body lumen within which the distal tip 65A is advanced. For example, a multi-region taper may be made shorter than a simple taper while producing similar or lower axial puncture forces, or a multi-region taper may be made equivalent in length to a simple taper while producing lower axial puncture forces.

Optionally, the distal-most region 65A-1 may be formed from desired materials for the dilator 60A, such as those described elsewhere herein, optionally without any external coating, and the adjacent region 65A-2 may be formed from the same or different materials than the distal-most region 65A-1, but with an external coating, as shown, e.g., a hydrophilic and/or lubricious coating.

Additionally, where the relatively steeper angle of the distal-most region 65A-1 may generate greater axial dilation forces, the diameter D2 may be set within the elastic range of the tissue being dilated, and the more shallow angle and/or coating of the adjacent region 65A-2 may reduce the axial dilation forces, e.g., to provide a net effect that substantially homogenizes the overall axial force encountered by the user when the dilator 60A is advanced through a puncture to dilate tissue surrounding the puncture, as described elsewhere herein.

It will be appreciated that more than two substantially linear tapered regions may be provided on the distal tip 65A, if desired, with each region having a smaller taper angle (relative to the longitudinal axis 68) and/or longer length than the distally adjacent region. As shown, the tapered regions may be disposed immediately adjacent one another. Alternatively, if desired, a substantially uniform diameter region (not shown) may be provided between differently tapered regions.

Turning to FIG. 5B, another embodiment of a distal end 64B of a dilator 60B is shown that includes a more complex design for the tapered distal tip 65B. In this embodiment, the distal tip 65B includes a continuously variable curve, which may vary substantially smoothly along the length of the distal tip 65B, e.g., according to the specific tissue dilation forces of target tissue. Optionally, the geometric force transforming elements provided by the complex tapered distal tip may be further enhanced or normalized, e.g., by providing one or more coatings and/or material layers, including hydrophobic and hydrophilic materials. For example, an area of relatively high tissue dilation force may be normalized (e.g., relative to the initial elastic range) by the addition of these coatings or materials and/or via a geometric transformation.

Figure 6A:
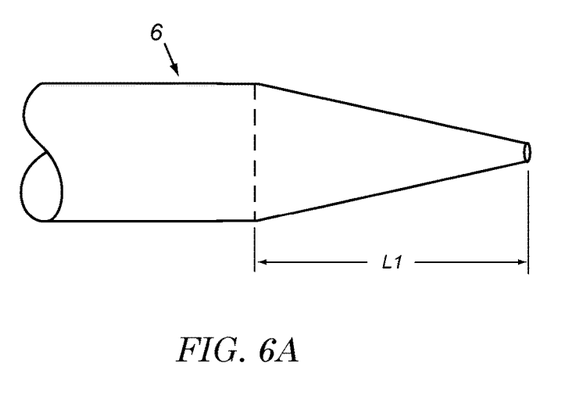
FIGS. 6A and 6B are details comparing the distal tip of FIG. 5A with a simple tapered distal tip.
Figure 6B:
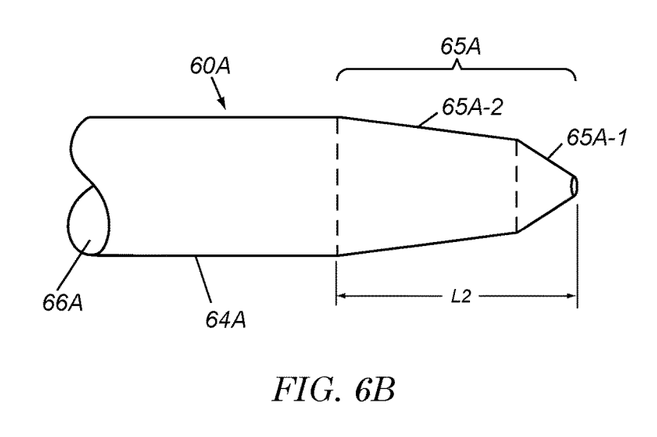

Turning to FIGS. 6A and 6B, a complex shaped distal tip of a dilator 60A (shown in FIG. 6B) is compared to a single taper tip 6 of a conventional dilator (shown in FIG. 6A). FIGS. 6A(1)-6B(2) show graphs demonstrating qualitatively the forces likely encountered when using the respective dilator tips to dilate a puncture through tissue. For example, FIG. 6A(1) demonstrates that the axial dilation force necessary to use the dilator tip 6 to dilate a puncture increases significantly as the single taper tip 6 is advanced through the tissue, e.g., due to the increasing resistance of the tissue to dilation after its initial elastic range. In contrast, FIG. 6A(2) demonstrates that the axial dilation force using the dilator 60A may be more consistent as the complex tapered tip 65A is advanced through the tissue, e.g., with the relatively shallow taper of the adjacent region 65A-2 requiring a substantially lower force than the single taper tip.

Similarly, FIGS. 6B(1) and 6B(2) demonstrate that the risk of "jumping" or over-advancement of the dilator 60A may be substantially reduced compared to the single taper tip 6. For example, once the single taper tip 6 completely exits the puncture, the resistance to advancement may be substantially reduced due to the uniform profile of the adjacent region. This unexpected change may cause the user to advance the dilator 6 substantially before being able to reduce the axial force. In contrast, given the shallow taper of the adjacent region 65A-2 of the complex dilator tip 65A, the change in resistance to advancement when the distal tip 65A completely exits the puncture may be less, thereby reducing the risk of the user over-advancing the distal tip 65A.

Figure 7:
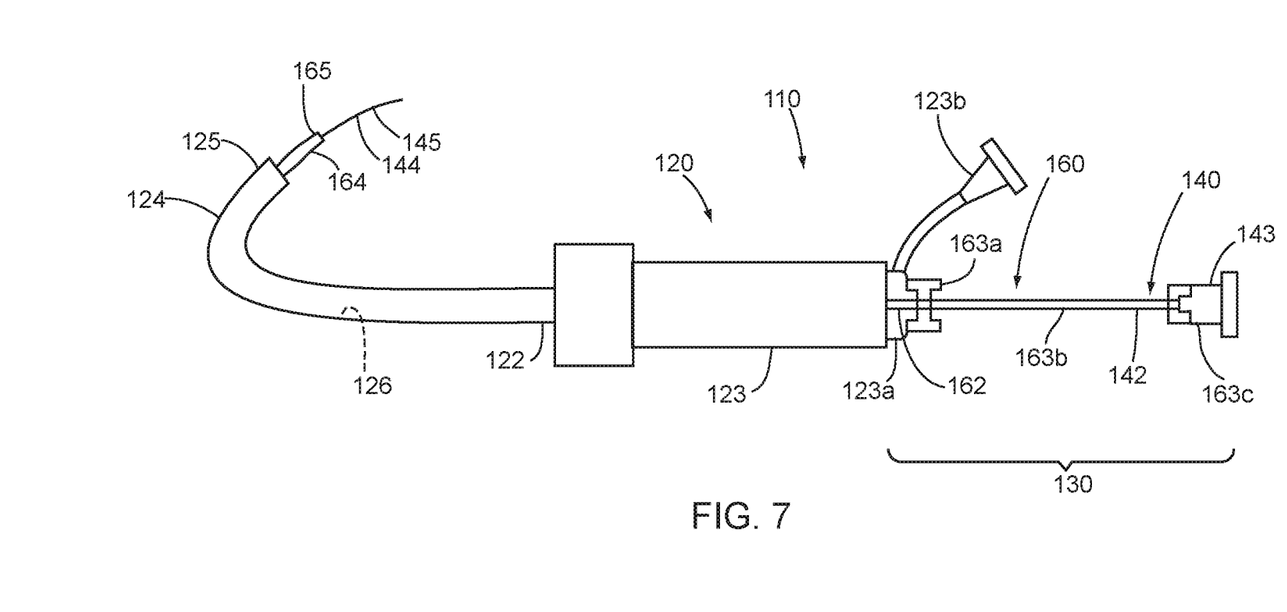
FIG. 7 is a side view of another exemplary embodiment of a system for performing a medical procedure using a trans-septal approach that includes a guide sheath, dilator, and needle.
Figure 8A:
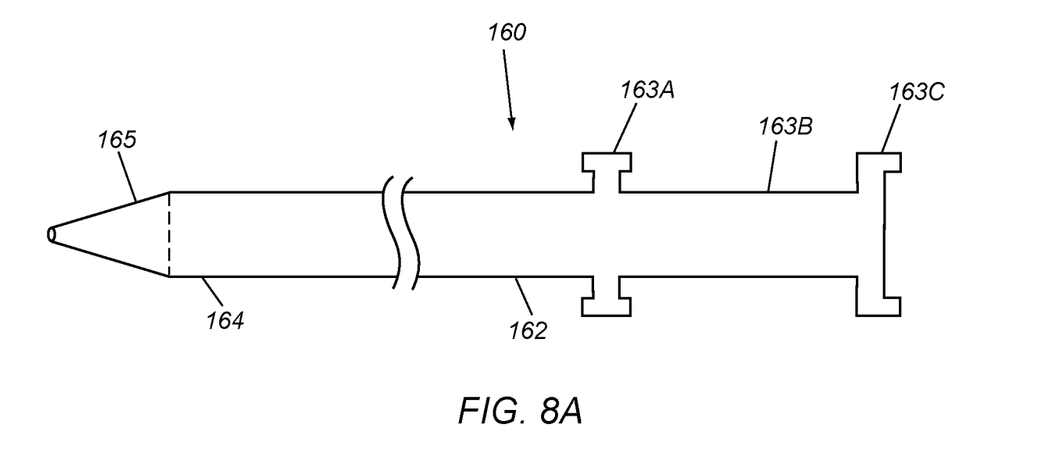
FIGS. 8A and 8B are side views of alternative embodiments of dilators that may be included in the system of FIG. 7.
Figure 8B:
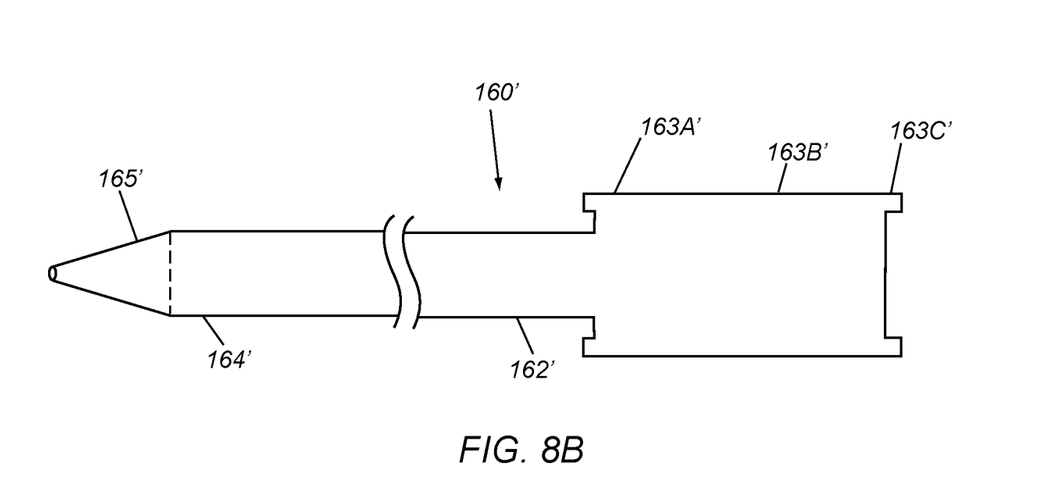

Turning to FIG. 7, another exemplary embodiment of a system 110 is shown that includes a guide sheath 120 and an access device 130, e.g., including a dilator 160 and a needle device 140, generally similar to other embodiments herein. Unlike other embodiments, the dilator 160 includes one or more stops and/or interlock elements 163, e.g., for selectively coupling the dilator 160 to the guide sheath 120 and/or the needle device 140. This may, for example, allow the length of the guide sheath 120 to be made shorter, e.g., for length compatibility with delivery of specific devices (e.g., balloon catheters, ablation catheters, and the like, not shown), while preserving length compatibility of the dilator 160 with a generally longer needle device 140, and/or with commonly available puncture devices, including Brockenbrough needles, RF puncture devices, and the like (also not shown).

Figure 9A:
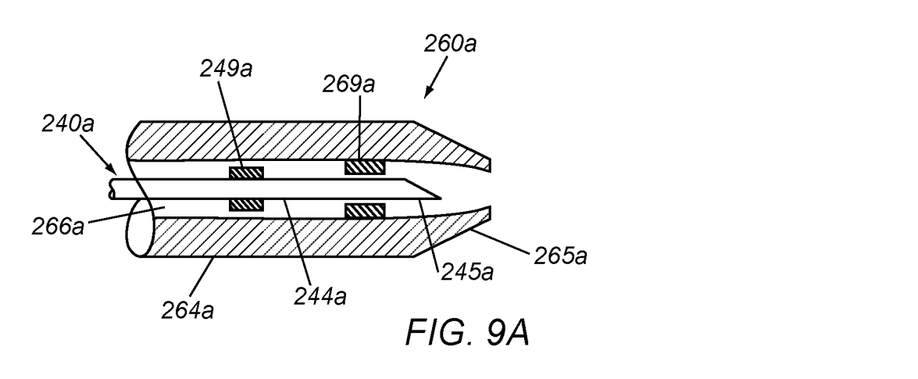
FIGS. 9A-9C are cross-sectional details of alternative embodiments of dilator-needle devices including different configurations of cooperating stops on the dilator and needle.

Optionally, in any of the embodiments herein, one or more stops may be provided for limiting relative motion of a needle and dilator, e.g., when the needle is used to create a puncture through a tissue structure. For example, as shown in FIG. 9A, shows an exemplary embodiment of an access device including a needle 240 and a dilator 260, which may be generally constructed and used similar to other embodiment herein. Unlike other embodiments, the needle 240 and dilator 260 include stops 249a, 269a fixed at predetermined locations thereon. For example, an annular stop 269a may be provided within the dilator lumen 266a, e.g., spaced proximally from the dilator distal tip 265a by a predetermined distance. Similarly, the needle 240 may include an annular stop 249a spaced proximally from the needle distal tip 245a. The stops 249a, 269a may be attached to the needle 240a and dilator 260a by one or more of bonding with adhesive, fusing, sonic welding, soldering, cooperating connectors (not shown), and the like, or may be integrally formed therein.

The stops 249a, 269a may be positioned to limit the distance that the needle distal tip 245a may be advanced from the dilator lumen 266a. For example, with the stops, a user may advance the needle 240a rapidly relative to the dilator 260a, e.g. to enhance puncturing the needle distal tip 245a through a tissue wall with the stops 249a, 269a preventing the distal tip 245a from being over-advanced into the body lumen beyond the tissue wall Optionally, at least one of the stops may be adjustable, e.g., to allow a user to adjust the deployment distance of the needle. For example, FIG. 9C shows another embodiment of a needle 240c and dilator 260c in which the stop 249c on the needle 240c is adjustable axially relative to the needle distal end 244c. For example, the needle 240c and stop 249c may include cooperating threads 284c that allow the stop 249c to be threaded axially along the needle distal end 244c, e.g., between predetermined proximal and distal positions. For example, the needle 240c may be rotated relative to the stop 249c (which may be movable axially but not rotatable within the dilator lumen 266c), thereby threading the stop 249c along the needle distal end 244c.

Figure 9B:
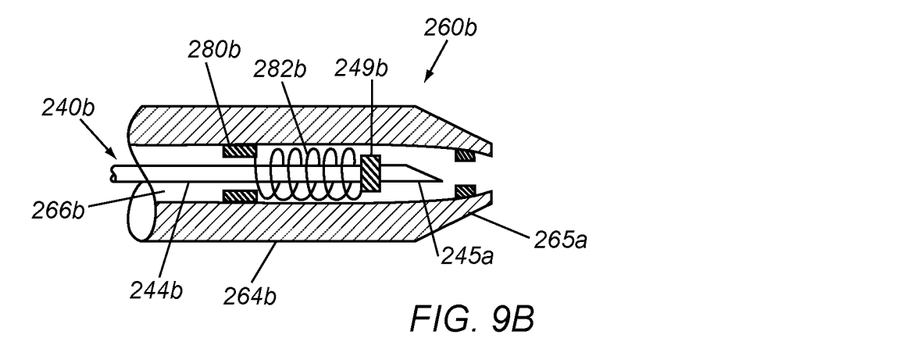
Figure 9C:
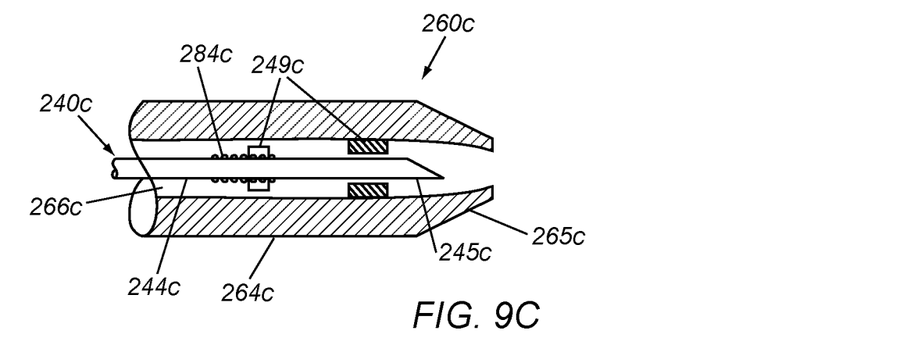

Turning to FIG. 9B, another embodiment of a needle 240b and dilator 260b that may include cooperating stops 249b, 269b similar to the other embodiments above. In addition, the needle 240b and dilator 260b may include an impulse device, e.g., a spring 282b coupled between the needle 240b and dilator 260b, e.g., between the needle stop 249b and an anchor 280b on the dilator 260b. The spring 282b may be used to eject the needle distal tip 245b from the dilator 260b, e.g., with the stops 249b, 269b limiting the distance that the needle distal tip 245b is deployed. For example, the needle 240b may be directed proximally to compress the spring 282b and store a predetermined level of potential energy such that, when the needle 240b is released, the spring 282b may be deploy the needle distal tip 245b from the dilator 260b with sufficient force to puncture entirely through a tissue wall, while the stops 249b, 269b prevent the needle distal tip 245b from being deployed beyond the predetermined distance, thereby reducing the risk of accidentally contacting undesired tissue with the needle distal tip 245b. It will be appreciated that these different configurations of stops and/or impulse devices may be included in any of the embodiments described herein.

The foregoing disclosure of the exemplary embodiments has been presented for purposes of illustration and description. It is not intended to be exhaustive or to limit the invention to the precise forms disclosed. Many variations and modifications of the embodiments described herein will be apparent to one of ordinary skill in the art in light of the above disclosure.

Further, in describing representative embodiments, the specification may have presented the method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A method for performing a medical procedure within a patient's body, comprising:
   introducing a distal end of a tubular sheath into a first body lumen;
   advancing a distal end of an outer tube from the distal end of the sheath within the first body lumen;
   pressing the outer tube distal end against a tissue wall within the first body lumen;
   with an inner needle positioned within the outer tube such that a sharpened distal tip of the needle is positioned adjacent the outer tube distal end and the tissue wall, retracting the outer tube, thereby impaling the tissue wall on the sharpened distal tip and directing the sharpened distal tip through the tissue wall into a second body lumen and creating a puncture through the tissue wall; and
   advancing the outer tube distal end over the needle through the puncture and into the second body lumen.

2. The method of claim 1, further comprising:
   advancing a dilator over the outer tube through the tissue wall, thereby dilating tissue surrounding the puncture;
   advancing the sheath distal end over the dilator through the dilated puncture into the second body lumen; and
   introducing one or more instruments through the sheath into the second body lumen to perform a medical procedure.

3. The method of claim 1, further comprising:
   removing the needle from the outer tube after advancing the outer tube distal end over the needle; and
   introducing a distal end of a guidewire through the outer tube into the second body lumen.

4. The method of claim 1, wherein the first body lumen is a right atrium of the patient's heart and the second body lumen is a left atrium of the patient's heart.

5. A method for performing a medical procedure within a patient's body, comprising:
   introducing a distal end of a tubular sheath into a first body lumen;

advancing a distal end of a needle device from the distal end of the sheath through a tissue wall into a second body lumen thereby creating a puncture through the tissue wall;

advancing a distal end of a dilator over the needle device through the tissue wall, thereby dilating tissue surrounding the puncture using a complex shaped tapered distal tip of the dilator; and advancing the sheath distal end over the dilator through the dilated puncture into the second body lumen, wherein the complex shaped tapered distal tip comprises a distal-most region having a first linear taper defining a first angle relative to a longitudinal axis of the dilator, and a second region adjacent the distal-most region having a second linear taper defining a second angle relative to the longitudinal axis, the second angle being smaller than the first angle to provide a substantially consistent axial dilation force when the complex shaped tapered distal tip is advanced through the tissue wall to dilate the puncture, and wherein the distal-most region is without an external coating, and the second region includes an external coating to reduce an axial force to advance the second region through the tissue wall.

6. The method of claim 5, further comprising introducing one or more instruments through the sheath into the second body lumen to perform a medical procedure.

7. The method of claim 6, further comprising removing the dilator and needle device from the sheath before introducing the one or more instruments.

8. The method of claim 5, wherein the needle device comprises a stop that limits advancement of the needle distal end beyond the sheath distal end to a predetermined distance.

9. The method of claim 8, further comprising adjusting the stop to set the predetermined distance before advancing the distal end of the dilator through the tissue wall.

10. The method of claim 5, wherein the needle device comprises an impulse device for applying a predetermined distal force to the needle distal end to puncture the needle distal end through the tissue wall and limit advancement of the needle distal end to a predetermined distance beyond the sheath distal end.

11. A method for performing a medical procedure within a patient's body, comprising:

introducing a distal end of a tubular sheath into a first body lumen;

advancing a distal end of a needle device from the distal end of the sheath through a tissue wall into a second body lumen to create a puncture through the tissue wall;

advancing a distal end of a dilator over the needle device through the tissue wall to dilate tissue surrounding the puncture using a complex shaped tapered distal tip of the dilator that generates a substantially constant axial dilation force as the distal tip is advanced through the tissue wall; and advancing the sheath distal end over the dilator through the dilated puncture into the second body lumen, wherein the complex shaped taper comprises a distal-most region having a first linear taper defining a first angle relative to a longitudinal axis of the dilator, and a second region adjacent the distal-most region having a second linear taper defining a second angle relative to the longitudinal axis, the second angle being smaller than the first angle to provide the substantially constant axial dilation force when the complex shaped tapered distal tip is advanced through the tissue wall to dilate the puncture, and wherein the distal-most region is without an external coating, and the second region includes an external coating to reduce an axial force to advance the second region through the tissue wall.

12. The method of claim 11, further comprising introducing one or more instruments through the sheath into the second body lumen to perform a medical procedure.

13. The method of claim 12, further comprising removing the dilator and needle device from the sheath before introducing the one or more instruments.

14. The method of claim 11, wherein the complex shaped tapered distal tip minimizes a change in resistance to advancement when the distal tip completely exits the tissue wall puncture, thereby reducing the risk of the user over-advancing the distal end of the dilator.

15. The method of claim 11, wherein the needle device comprises a stop that limits advancement of the needle distal end beyond the sheath distal end to a predetermined distance.

16. The method of claim 15, further comprising adjusting the stop to set the predetermined distance before advancing the distal end of the dilator through the tissue wall.

17. The method of claim 11, wherein the needle device comprises an impulse device for applying a predetermined distal force to the needle distal end to puncture the needle distal end through the tissue wall and limit advancement of the needle distal end to a predetermined distance beyond the sheath distal end.

* * * * *